(12) United States Patent
Park et al.

(10) Patent No.: US 10,632,049 B2
(45) Date of Patent: Apr. 28, 2020

(54) COSMETIC COMPRISING LOW VISCOSITY COSMETIC INGREDIENTS

(71) Applicant: LG HOUSEHOLD & HEALTH CARE LTD., Seoul (KR)

(72) Inventors: Byeong-Gyu Park, Daejeon (KR); Sung-Soo Kang, Daejeon (KR); Min-Ji Cha, Daejeon (KR); Sang-Wook Park, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 76 days.

(21) Appl. No.: 15/103,089

(22) PCT Filed: Apr. 7, 2016

(86) PCT No.: PCT/KR2016/003670
§ 371 (c)(1),
(2) Date: Jun. 9, 2016

(87) PCT Pub. No.: WO2016/200038
PCT Pub. Date: Dec. 15, 2016

(65) Prior Publication Data
US 2017/0119633 A1    May 4, 2017

(30) Foreign Application Priority Data

Jun. 12, 2015  (KR) .................. 10-2015-0083109
Oct. 21, 2015  (KR) .................. 10-2015-0146471

(51) Int. Cl.
*A61K 8/06*     (2006.01)
*A61Q 19/00*    (2006.01)
(Continued)

(52) U.S. Cl.
CPC ............ *A61K 8/064* (2013.01); *A45D 33/006* (2013.01); *A45D 34/00* (2013.01); *A45D 34/04* (2013.01);
(Continued)

(58) Field of Classification Search
None
See application file for complete search history.

(56) References Cited

U.S. PATENT DOCUMENTS

| | | | |
|---|---|---|---|
| 5,107,871 A * | 4/1992 | Butcher | A45D 33/006 132/293 |
| 5,865,194 A | 2/1999 | Gueret | 132/299 |

(Continued)

FOREIGN PATENT DOCUMENTS

| | | | |
|---|---|---|---|
| CN | 101438883 | 5/2009 | ............. A45D 33/02 |
| CN | 104363888 | 2/2015 | ............. A45D 37/00 |

(Continued)

OTHER PUBLICATIONS

English translation (2017) of KR1020130039987 (2013).*
(Continued)

*Primary Examiner* — Patricia Duffy
*Assistant Examiner* — Garen Gotfredson
(74) *Attorney, Agent, or Firm* — Harness, Dickey & Pierce, P.L.C.

(57) ABSTRACT

The present disclosure provides a cosmetic including a cosmetic composition having low viscosity, a receiving member in which the cosmetic composition having low viscosity is received, and a film forming member which covers an opening of the receiving member. By the use of the elastic film forming member, the cosmetic of the present disclosure may provide convenience of carrying with, reduce the container volume, and increase an amount of (Continued)

cosmetic composition contained, as compared to sponge impregnation material cosmetics.

11 Claims, 3 Drawing Sheets

(51) Int. Cl.
*A61K 8/02* (2006.01)
*A45D 34/04* (2006.01)
*A61Q 1/02* (2006.01)
*A45D 34/00* (2006.01)
*A45D 33/00* (2006.01)

(52) U.S. Cl.
CPC .............. *A61K 8/02* (2013.01); *A61K 8/0208* (2013.01); *A61Q 1/02* (2013.01); *A61Q 19/00* (2013.01); *A45D 2200/1009* (2013.01); *A61K 2800/87* (2013.01)

(56) References Cited

U.S. PATENT DOCUMENTS

| | | | |
|---|---|---|---|
| 9,532,934 B2 | 1/2017 | Choi et al. | ............. A61K 8/046 |
| 2007/0212401 A1* | 9/2007 | Masse | .................. A61K 8/0208 |
| | | | 424/443 |
| 2009/0126759 A1 | 5/2009 | Balestrini | ..................... 132/307 |
| 2012/0070685 A1* | 3/2012 | Kloss | ....................... C23C 14/20 |
| | | | 428/626 |
| 2015/0079862 A1* | 3/2015 | Jeong | ..................... A45D 34/00 |
| | | | 442/1 |
| 2016/0353857 A1* | 12/2016 | Kim | ..................... A45D 33/008 |

FOREIGN PATENT DOCUMENTS

| | | | |
|---|---|---|---|
| CN | 104379124 A | 2/2015 | |
| JP | 2895017 | 5/1999 | ............. A45D 33/00 |
| JP | 2002-010827 | 1/2002 | ............. A45D 33/00 |
| JP | 2008194190 A * | 8/2008 | |
| JP | 2015-513987 | 5/2015 | ............. A45D 33/00 |
| KR | 10-1112477 | 2/2012 | ............. A45D 34/00 |
| KR | 10-2012-0108509 | 10/2012 | ............. A61K 8/87 |
| KR | 10-1380587 | 3/2014 | ............. A45D 34/00 |
| KR | 20-0473939 | 8/2014 | ............. A45D 34/00 |
| KR | 10-1477583 | 12/2014 | ............. A45D 34/00 |
| KR | 20-2015-0001844 | 5/2015 | ............. A45D 34/04 |
| TW | M488241 U | 10/2014 | |
| WO | WO 2015-060589 | 4/2015 | ............. A45D 34/00 |

OTHER PUBLICATIONS

English translation of JP2008194190A (Oct. 15, 2019).*
First Korean Office Action dated Nov. 18, 2015 issued in KR 10-2015-0146471, with English translation.
Second Korean Office Action dated Mar. 9, 2016 issued in KR 10-2015-0146471, with English translation.
Notice of Allowance dated Mar. 17, 2016 issued in KR 10-2015-0146471, with English translation.

* cited by examiner

COSMETIC COMPRISING LOW VISCOSITY COSMETIC INGREDIENTS

CROSS-REFERENCE TO RELATED APPLICATIONS

This application is a national phase application of PCT Application No. PCT/KR2016/003670, filed on 7 Apr. 2016, which claims benefit of Korean Patent Application Nos. KR 10-2015-0146471 filed 21 Oct. 2015 and KR 10-2015-0083109 filed 12 Jun. 2015. The entire disclosures of the applications identified in this paragraph are incorporated herein by references.

FIELD

The present disclosure relates to a cosmetic comprising a low-viscosity flowable cosmetic composition, and more particularly, to a cosmetic in which a low-viscosity cosmetic composition with high flowability is stored and dispensed through sheet-type elastic film forming member.

BACKGROUND

The inventors found that low viscosity cosmetic ingredients have higher spreadability when used and better moisturized feeling and provide generally higher makeup satisfaction to customers than high viscosity cosmetic ingredients, and they have made many attempts to develop products that are convenient for carrying with and using. In cushion products that are popular in cosmetics these days, low-viscosity flowable cosmetic ingredients are primarily used, and to contain the low-viscosity content, sponge type impregnation materials are used.

Sponge impregnation materials such as Korean Patent Publication No. 10-2012-0108509 (cosmetic including urethane foam impregnated with cosmetic composition) are designed for content storage and convenient use, but because a specific surface area occupied by a sponge is large, to increase an amount of cosmetic ingredients, a container increases in size and a large amount of cosmetic ingredient residues is generated, making it difficult for customers to reasonably use it, and as the content reduces with the continuous use, the cosmetic ingredients are not easily dispensed from the sponge, consequently reducing the makeup effect. In addition, it was found that miniaturization of the container reduces the capacity to hold the content.

To provide a compact container having an increased capacity to hold the content, as in Korean Patent No. 10-1380587 (elastic discharge spigot for flowable cosmetic ingredients), embossing treatment and relief carving on an elastic discharge spigot was used, but the relief carving alone is insufficient to prevent the low-viscosity flowable content from leaking out due to impacts when being transported or carried, and in use, the content remains between the embossed patterns due to the surface embossing, so the surface gets dirty or contaminated and a large amount of residues is generated.

On the other hand, Korean Patent No. 10-1477583 discloses a portable cosmetic with a mesh part to store liquid or gel cosmetic ingredients, but the cosmetic contained is required to have an optimum viscosity of 20,000 to 40,000 cPs in consideration of portability and storage. That is, when the viscosity is below the range, it is difficult to store.

DISCLOSURE

Technical Problem

To solve the problem such as the above, the present disclosure is directed to providing a new type of cosmetic that is convenient to carry with and use and can hold the low viscosity content.

The present disclosure is directed to providing a cosmetic that is convenient to carry with due to an excellent liquid holding capacity, increases an amount of cosmetic ingredients contained therein, and allows for easy dispensing by an external force when used, greatly reducing an amount of cosmetic ingredient residues.

The present disclosure is directed to providing a cosmetic provided with a sieve-type member having excellent elasticity and excellent shape recovery capability to always maintain appearance to look as if for the first time and provide an excellent makeup effect during continuous use.

The present disclosure is directed to providing a new type of cosmetic that may replace a conventional sponge impregnation material having a large specific surface area, as a result of which the container size increases or an amount of cosmetic ingredients contained reduces to hold the low viscosity content.

The present disclosure is directed to providing a new type of cosmetic easy to store a cosmetic composition having high flowability that may effectively dispense the content while preventing leakage of the content from the cosmetic.

Technical Solution

To achieve the above objects, the present disclosure provides a cosmetic 1 including a cosmetic composition film forming member 30 to cover an opening 12 of a receiving member 10 in which a low viscosity cosmetic composition 20 is received. In impregnation material cosmetics, because a specific surface area occupied by an impregnation material is large, the container size increases to hold a larger amount of cosmetic ingredients and an amount of contents received reduces to achieve the compact container design. In this circumstance, to solve the problem, the present disclosure provides a low viscosity cosmetic composition and a cosmetic in which the cosmetic composition is dispensed through a film forming member.

The present disclosure may effectively store low viscosity cosmetic ingredients through a member that forms a water film or oil film on the surface of the cosmetic ingredients, thereby reducing the container size or increasing an amount of cosmetic ingredients received. In addition, there are provided the cosmetic 1 that may minimize an amount of residues and provide an excellent makeup effect during continuous use.

The low viscosity cosmetic composition 20 as used herein refers to a flowable cosmetic composition, and typically includes liquid (fluid) cosmetic ingredients. Currently, to hold low viscosity (7,000 cPs or less) cosmetic ingredients having high flowability in the form of a pact convenient to carry with, a sponge-type impregnation material having a large specific surface area or an airless pact-type container has been used. After pondering upon the above problem, the inventors found that the film forming member 30 having the water/oil absorbing capability forms a water film or oil film and even the content having low viscosity and high flowability is stored in the pact container well when being carried or transported, and is dispensed well when used, and completed the present disclosure.

The low viscosity cosmetic composition 20 in the present disclosure have viscosity in the range of 1,000 cPs to 7,000 cPs as measured with Brookfield Synchro-Lectric Viscometer (USA) at 30 RPM for 1 minute using spindle #4, and when the viscosity is less than 1,000 cPs, the liquid content holding capability reduces, causing a leakage problem, and when the viscosity is higher than 7,000 cPs, the overall makeup satisfaction is low, such as including spreadability and moisturized feeling that are advantages of the low viscosity cosmetic ingredients. Accordingly, the viscosity is in the range of 1,000 cPs to 7,000 cPs, and preferably in the range of 2,000 cPs to 6,000 cPs.

When the viscosity of the cosmetic composition is less than 10,000 cPs, the content leakage problem occurs due to flowability of a liquid unless the container is air-tightly sealed, and to solve the problem, an impregnation material such as a sponge has been used to carry with a cosmetic composition having the above range in the field of industry. In contrast, the inventors provide a method for carrying with a cosmetic composition less than 10,000 cPs in a simple and convenient manner by employing the film forming member 30 through the present disclosure.

The film forming member of the present disclosure may be a reticulated structure having elasticity.

The term elasticity refers to the quality that deforms when an external force is applied and restores to an original shape when the external force is removed. For example, elasticity of the present disclosure refers to the capability to restore an original shape when removing a force that has been applied to the film forming member down to the bottom surface of the receiving member 10.

The substantial restoring capability may include the degree of recovery of about 70% of an original shape, preferably about 80%, and more preferably 90% or more.

The reticulated structure of the present disclosure includes many passages to allow dispensing or discharging as well as having the liquid holding capacity to hold the cosmetic composition, and covers all types that allow the content to be dispensed through grids formed by fibers. For example, the type such as a net and a mesh may be included in the range of reticulated structure of the present disclosure.

The inventors found that the film forming member affects the water film or oil film according to the formulation of the low viscosity cosmetic composition 20. Specifically, it was found that the film forming member may prevent the leakage of the cosmetic composition and stably store the cosmetic composition in the receiving member 10, as well as allowing easy dispensing of the content by the pressure when used. It is thought that this is because the film forming member 30 affects the tension of the oil film or water film of the cosmetic composition by a contact with the interface of the low viscosity cosmetic composition 20, but it is not construed as being limited to this theory.

Preferably, the film forming member may be in sheet like paper with the entire thickness in the range of 0.4 mm to 3 mm, and may be used in one layer or two or more layers. Materials for the film forming member may be fibers, foam rubbers and polyurethane foams, and may be used in one layer or two or more layers, and it is preferred to use a fiber fabric made of fibers having an excellent recovery capability, and even though a fabric is densely woven, if the entire thickness is less than 0.4 mm, the liquid content holding capacity is low, causing the content spilling problem when the container stands upside down or upright, and if the entire thickness is more than 3 mm, it is impossible to reduce the container size or increase an amount of contents in order to improve portability and convenience that has been intended to be achieved and an amount of residues increases, and accordingly, the range of 0.4 mm to 3.0 mm, and preferably the range of 0.6 mm to 2 mm is desirable.

The "film" in the film forming member of the present disclosure may be used to include not only a water film or oil film of the cosmetic composition formed by interfacial tension and attraction generated on the surface of the cosmetic composition, but also a surface film created by impregnation into the member.

By the film forming member of the present disclosure, a film of the cosmetic composition may be formed, and by the film formed on the cosmetic composition and the cosmetic composition film forming member, the cosmetic composition may be maintained well without leaks.

In the present disclosure, in addition to the thickness of the film forming member, the pore size and elasticity may affect the formation of the water film or oil film.

To store the content well and accomplish good transfer when used, the larger thickness and the smaller pore size with the optimum water or oil absorbing capability contributes to excellent content storing capability, and elasticity is preferably selected to ensure excellent performance characteristics during use and reduce an amount of residues according to the properties of the content and the depth of the container by controlling a fiber weaving method, the type and thickness of fibers or a blending method to allow the sheet-type film forming member to restore to an original shape after used. Further, the surface characteristics of the fibers may be modified by coating the yarns or the fabric.

The "cosmetic composition film forming member" of the present disclosure has a support function for preventing the leakage of the cosmetic composition, and a function that allows the content to be dispensed with the increasing pore size by a force pressing down and disallows the dispensing of the content with the decreasing pore size when the force is removed. That is, the inventors attempted to provide a revolutionary type of cosmetic outside the thought that 'cosmetic can be only received in a container with an air-tight structure due to leaks caused by low viscosity pores' commonly recognized in the art.

The cosmetic composition film forming member may act as a support in the respect that it prevents the leakage of the cosmetic composition, and perform a dispensing control function in the respect that dispensing is performed and stopped repeatedly by pore structure deformation.

The film forming member included in the present disclosure may be any one selected from the group consisting of a fiber fabric, a foam rubber sheet, a urethane foam sheet, and blends thereof.

The fiber fabric refers to a textile material made through processing of fibers, and consists of a collection of fibers. A fiber is a natural or artificial strand or thread of material that is significantly long and thin and can be softly bent, and is a natural fiber and an artificial fiber according to its production process. The natural fiber includes a plant fiber, an animal fiber, and a mineral fiber, and the plant fiber includes seed fiber such as cotton, kapok fiber and coier, leaf fiber such as manila hemp and saisal hemp, and bast fiber such as flax, ramie, jute and hemp, and the animal fiber includes wool and hair fiber such as wool, goat hair, camel hair and cashmere, and silk fiber such as cultivated silk and wild silk. Also, the mineral fiber includes rock wool (asbestos). The artificial fiber may be an inorganic fiber and an organic fiber, and the inorganic fiber includes metal fiber such as gold metallic yarn and silver metallic yarn, and silicate fiber such as glass fiber, rock fiber, and slag fiber. The organic fiber is a regenerated fiber, a semi-synthetic fiber, and a synthetic fiber. The regenerated fiber includes cellulose fiber such as viscose rayon and cupra rayon and protein fiber, the semi-synthetic fiber includes acetate and triacetate, and the synthetic fiber includes polyamide-based fiber such as nylon fiber, polyester-based fiber such as polyester fiber, polyurethane-based fiber, polyuria-based fiber, polyethylene-based fiber, polyvinyl chloride-based fiber, polyvinylidene-based fiber, polytetrafluoroethylene-based fiber, polyvinyl alcohol-based fiber, polyacrylonitrile-based fiber and polypropylene-based fiber, and these fibers may be used alone or in combination, and may be given elasticity allowing them to stretched according to a weaving method, preferably by blending with spandex that is a type of polyester-based fiber and polyurethane-based fiber.

An embodiment of the present disclosure produces a sheet type fabric using fibers and uses it as a cosmetic composition film forming member, and the fabric may be largely a woven fabric and a knit fabric by weaving, and a nonwoven fabric. The woven fabric is a textile formed by interfacing the warp (longitudinal thread) and weft (transverse thread) in a criss-cross pattern, and it is the most basic type of textile weave. A weave structure having many crossings is used for a strong fabric, and plain weave, twill weave, and satin weave according to a weaving method. In plain weave, warp and weft are aligned by the most simple and dense method and each weft crosses the warp. Many crossings contribute to production of a fabric which is strong and less sensitive to yarn slippage. Typical fabrics include fresco organdy, tafta and muslin. In twill weave, each of warp and weft floats across two or more yarns to produce diagonal lines. It is soft a bit and less prone to wrinkle. It is smooth, dense and durable depending on the weave structure and density. It includes denim, drill, gabardine, twill, tricotine, and serge. In satin weave, four or more warp yarns go over one weft at a regular interval, and it is smooth, uniform and sheeny. It includes satin, damask, and atlas.

As opposed to woven fabric made by aligning weft and warp criss-cross, knit fabric refers to a textile in which one continuous of yarn is looped one-on-one using a stick-like or hooked needle, and because the yarn strands intertwine below stitches, the fabric is undone back into one strand of yarn when unknitting the last stitch. Also, net, macrame and lace consisting of two or more intertwined yarns include techniques for knit fabrics. The knit fabric may be warp-knit fabric and weft-knit fabric, and the warp-knit fabric is a fabric in which yarn runs lengthwise (vertical direction), while the weft-knit fabric is a fabric in which yarn runs crosswise (horizontal direction). The two types differ in the entire process from a preparation operation to a fabric making operation including machine, but fabrics used for compression clothes or swimwear belong in warp-knit fabric, and knitwear belongs in a weft-knit fabric. For the sheet-type film forming member of the present disclosure, both woven fabric and knit fabric can be used.

The fabric of the present disclosure may include all types of fabrics no matter whether they are brushed or not.

In addition of the fiber fabric of the present disclosure, a foam rubber sheet, a polyurethane foam sheet, or blends thereof may be used for the cosmetic composition film forming member. Preferably, any one selected from a foam rubber sheet, a polyurethane foam sheet, and blends thereof may be used with the fiber fabric.

The foam rubbers or polyurethane foams include, but are not limited to, those generally used in the art for cosmetic composition impregnation, for example, any one selected from the group consisting of styrene-butadiene rubber (SBR), natural rubber (NR), butadiene rubber (BR), acrylonitrile-butadiene rubber (NBR), polyethylene (PE), polyvinyl alcohol (PVA), ethylene vinyl acetate (EVA) and blends thereof.

The polyurethane foams may be those obtained by foaming polyether urethane, polybutadiene urethane, polyester urethane or blends thereof singly or in combination, and all polyurethane foams generally used in the art fall within the scope of the present disclosure.

The foam rubbers that can be used for the film forming member are produced by foaming natural rubber, synthetic rubber or combinations thereof, and foaming may be performed using foaming agents and catalysts generally used in the art.

The natural rubber may be general natural rubber or modified natural rubber, and may include modified natural rubber. The natural rubber may generally include natural rubber (NR). Any material known as natural rubber may be used, and there is no particular limitation on the place of origin. The synthetic rubber may be any one selected from the group consisting of styrene butadiene rubber (SBR), modified styrene butadiene rubber, butadiene rubber (BR), modified butadiene rubber, chlorosulfonated polyethylene rubber, epichlorohydrin rubber, fluorocarbon rubber, silicone rubber, nitrile rubber, hydrogenated nitrile rubber, nitrile butadiene rubber (NBR), modified nitrile butadiene rubber, chlorinated polyethylene rubber, styrene butadiene styrene rubber (SBS), and blends thereof.

The cosmetic composition of the present disclosure fall within the scope of the present disclosure provided that it is a flowable cosmetic composition having the viscosity range as used herein, and there is no particular limitation on formulation.

The low viscosity cosmetic composition 20 may include pigments, antioxidants, activators, moisturizers, pharmaceuticals, metal ion sequestrants, polyalcohols, preservatives, and flavoring without detracting from the objects of the present disclosure, if necessary.

The cosmetic composition may be prepared by a general method in the art.

Advantageous Effects

The cosmetic with the film forming member of the cosmetic composition including the low viscosity cosmetic composition according to the present disclosure may form, maintain or create an oil film or a water film on the surface of the cosmetic ingredients according to the formulation.

By the use of the elastic film forming member, the cosmetic of the present disclosure may provide convenience of carrying with, reduce the container volume, and increase an amount of cosmetic composition contained, as compared to sponge impregnation material cosmetics.

In addition, the cosmetic of the present disclosure may allow for easy dispensing by an external force when used, greatly reduce an amount of cosmetic ingredient residues, and maintain a clean and neat appearance.

BRIEF DESCRIPTION OF THE DRAWINGS

Hereinafter, the present disclosure will be described in more detail through the following embodiments. However, the embodiments according to the present disclosure may be modified in many different forms, and the scope of the present disclosure shall not be construed as being limited to the embodiments described below. The embodiments of the present disclosure are provided for illustration to help a full understanding of the present disclosure.

(a) is a photographic image before a cosmetic composition is received in a receiving member.

(b) is a photographic image showing that a cosmetic composition is received in a receiving member.

(c) is a photographic image showing that a film forming member and a cosmetic composition bring into contact with each other.

Figure 1:
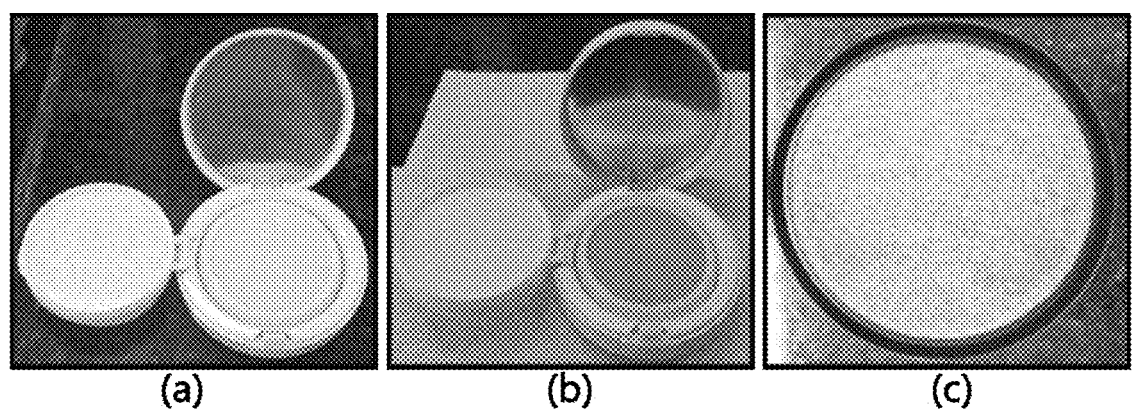
FIG. 1 is a photographic image illustrating a cosmetic of the present disclosure.
Figure 2:
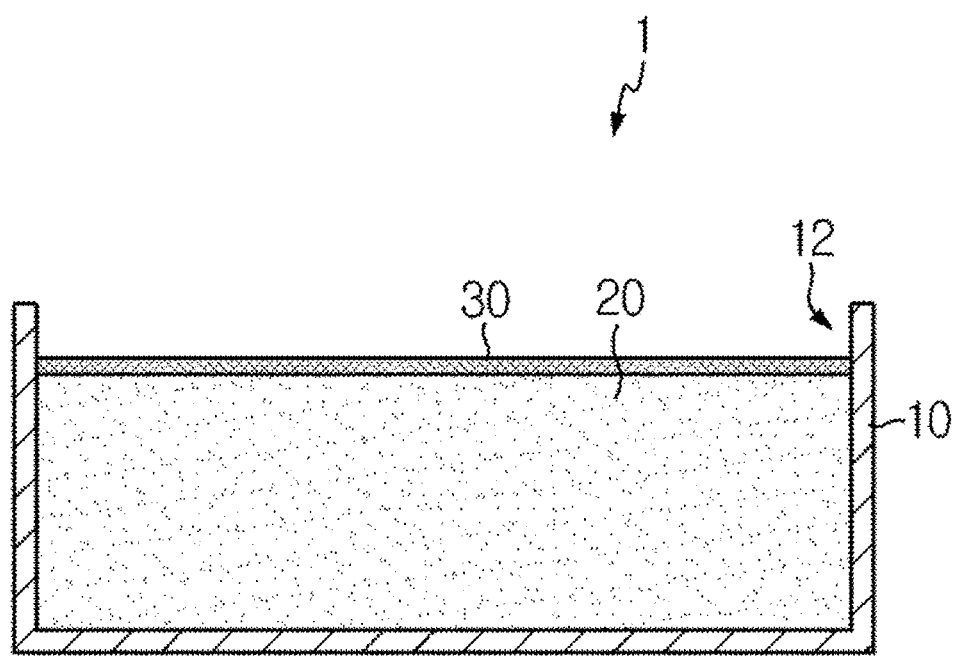

FIG. 2 is a diagram illustrating the structure of a cosmetic of the present disclosure.

Figure 3:
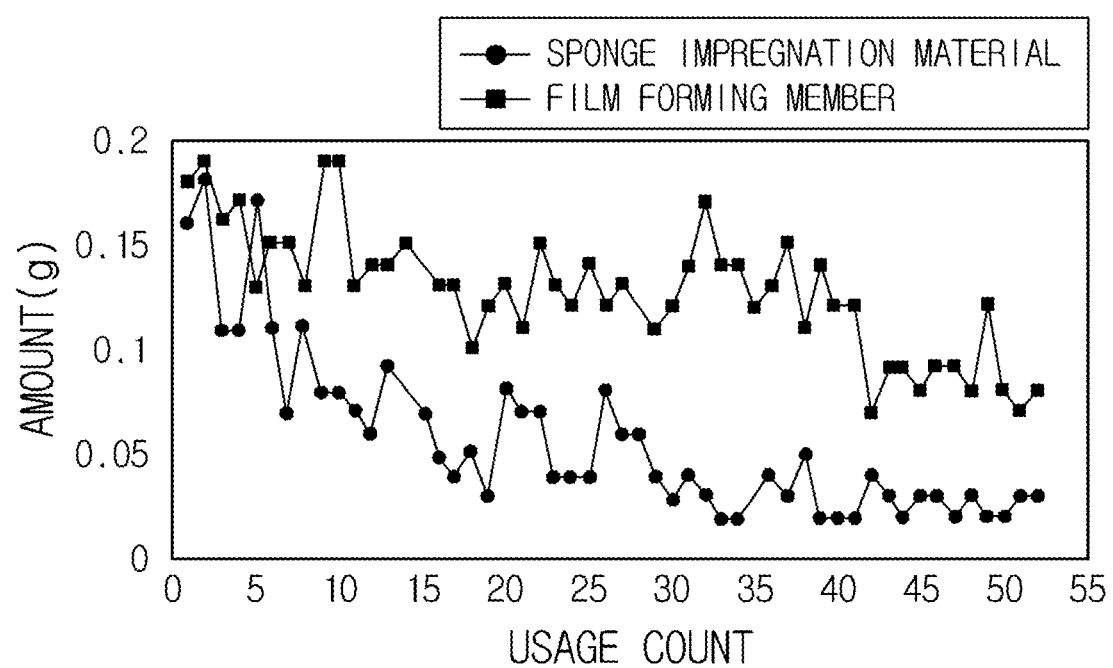

FIG. 3 is a result of comparing the quantity dispensed between a cosmetic of the present disclosure and a cosmetic using a sponge impregnation material.

BEST MODE

Hereinafter, the present disclosure will be described in detail with reference to examples and embodiments to aid in understanding the present disclosure. However, the examples and embodiments according to the present disclosure may be modified in many different forms, and the scope of the present disclosure shall not be construed as being limited to the examples and embodiments mentioned below. The examples and embodiments of the present disclosure are provided to help one having ordinary skill in the art understand the present disclosure more fully.

Water-in-oil type foundations were prepared with the components and amounts described in the following table 1.

Oil phase components and a thickening agent were put in an oil phase tank and heated to 80° C. to turn into a uniform state, and pigments were added and dispersed. Water phase components were put in a water phase tank and heated to 80° C. to completely dissolve the raw materials, and then were added to the oil phase tank containing the dispersed pigments, followed by emulsification using a homo mixer to prepare a low viscosity UV blocking emulsion. A 40 ml stabilization container was filled with the content and kept at a 25° C. chamber for one day or longer, and after operation of Brookfield LVII viscometer at 30 rpm for 1 minute using spindle #4, viscosity was measured at 25° C.

TABLE 1

| | | Amount (wt %) | | | | |
|---|---|---|---|---|---|---|
| Classification | Name of raw material | Example 1 | Example 2 | Example 3 | Comparative example 1 | Comparative example 2 |
| Oil phase component | Cyclopentasiloxane | 17.0 | 16.0 | 15.0 | 27.0 | 12.0 |
| | Hexyl laurate | 10.0 | 10.0 | 10.0 | 10.0 | 10.0 |
| | Caprylic/capric triglyceride | 2.0 | 2.0 | 2.0 | 2.0 | 2.0 |
| | Dimethicone | 2.0 | 2.0 | 2.0 | 2.0 | 2.0 |
| | Ethylhexylmethoxycinnamate | 7.0 | 7.0 | 7.0 | 7.0 | 7.0 |
| | PEG-10 dimethicone | 3.0 | 3.0 | 3.0 | 3.0 | 3.0 |
| | Bis-ethylhexyloxyphenolmethoxy-phenyltriazine | 1.5 | 1.5 | 1.5 | 1.5 | 1.5 |
| | Sorbitan sesquioleate | 0.5 | 0.5 | 0.5 | 0.5 | 0.5 |
| Thickening agent | Disteardimonium hectorite | Optimum amount | Optimum amount | Optimum amount | Optimum amount | Optimum amount |
| Pigment | Colored titanium dioxide | 9.0 | 9.0 | 9.0 | 9.0 | 6.0 |
| | Ultrafine titanium dioxide | 4.0 | 4.0 | 4.0 | 4.0 | 7.0 |
| | Mica | 2.0 | 2.0 | 2.0 | 2.0 | 2.0 |
| | Yellow iron oxide | 0.9 | 0.9 | 0.9 | 0.9 | 0.9 |
| | Red iron oxide | 0.2 | 0.2 | 0.2 | 0.2 | 0.2 |
| | Black iron oxide | 0.1 | 0.1 | 0.1 | 0.1 | 0.1 |
| Water phase | Water | to 100 | to 100 | to 100 | to 100 | to 100 |
| | Glycerin | 5.0 | 5.0 | 5.0 | 5.0 | 5.0 |
| | Salt | 1.0 | 1.0 | 1.0 | 1.0 | 1.0 |
| | Tromethamine | 1.6 | 1.6 | 1.6 | 1.6 | 1.6 |
| | Phenylbenzimidazole sulfonic acid | 2.7 | 2.7 | 2.7 | 2.7 | 2.7 |
| | Viscosity (cPs) | 1800 | 4,000 | 6,200 | 800 | 8,200 |

TABLE 2

| Sheet-type film forming member | Material | Thickness (mm) |
|---|---|---|
| Comparative example 3 | Nylon | 0.06 |
| Comparative example 4 | Polyester | 0.33 |
| Comparative example 5 | Polyester + Spandex | 0.22 |
| Comparative example 6 | Cotton | 3.28 |
| Example 4 | Polyester | 1.02 |
| Example 5 | Polyester + Spandex | 0.95 |
| Example 6 | Polyester + Spandex | 1.64 |
| Example 7 | Cotton + Spandex | 0.56 |

The thickness was measured using a vernier caliper (Model: BLUEBIRD DIGITAL CALIPER).

EXPERIMENTAL EVALUATION EXAMPLE

Using the low viscosity cosmetic composition prepared through examples 1, 2 and 3, a comparative experiment was made on a sponge impregnation material cosmetic ingredients and a low viscosity cosmetic composition stored in a receiving member with a sheet-type film forming member without using a sponge.

In the case of a sponge impregnation material, a cushion-type container (Pumtech) and a sponge (Coreapuff) available on the market were used, and for the receiving member of the present disclosure, the same container as a container containing a sponge impregnation material impregnated with a cosmetic composition was used, and for the sheet-type film forming member of the present disclosure, those of examples 4-7 were used.

Experimental Example 1: Test of an Amount of Contents Filled and an Amount of Residues In the case of an amount of contents filled, after the sponge impregnation material was impregnated with the content of example 2 in the same container, and stored in the receiving member with the sheet-type film forming member (example 5 applied), the weight at the time when the flow or leakage of the content in the container standing upright does not occur was measured and compared, and in the case of an amount of residues, after the same container was filled with 15 g, followed by impregnation, twenty female customers in their twenties to forties were allowed to use by a method of using the content using a puff until it is impossible to apply makeup, and a ratio of the amount of residues was measured and averaged.

TABLE 3

|  | Amount of contents filled (g) | Amount of residues (%) |
|---|---|---|
| Sponge impregnation material cosmetic ingredients | 16.28 | 28.3 |
| Cosmetic composition stored in a receiving member with a sheet-type film forming member | 20.42 | 13.3 |

As a result, as can be seen from Table 3, in the case of the present disclosure, an amount of contents filled is large, enabling compact container design for the same amount of contents filled, and an amount of residues is low during use to allow customers to use a larger amount of contents, resulting in economic efficiency.

Experimental Example 2: Test of Amount of Contents Dispensed

In the case of the impregnation material cosmetic ingredients, the content needs to be transferred from the impregnation material surface to the puff well for customers' convenient use. After the sponge impregnation material was impregnated with the content of example 2 and 15 g of the content of example 2 was stored in a cosmetic with the sheet-type film forming member of example 5, twenty female customers in their twenties to forties were allowed to use using a ruby cell puff, and an amount of transfer to the puff each time they use was measured and compared in the form of a graph as shown in FIG. 3. As an amount of contents filled and a deviation were too large in each customer for the first five times of use, an amount of contents used was measured and averaged according to the usage count from the sixth use.

As a result, as shown in FIG. 3, as the usage count increases, the cosmetic of the present disclosure has a higher quantity dispensed and a smaller reduction width relative to an initial quantity dispensed than the cosmetic including the sponge impregnation material, and thus, an advantage is that convenient makeup is achieved during continuous use.

Experimental Example 3: Test of Sensorial Feeling and Makeup Effect

Using the content of example 2, to conduct a comparative experiment for makeup effect and sensorial feeling on the sponge impregnation material cosmetic ingredients (A) and the cosmetic (B) including the sheet-type film forming member (example 5 applied), twenty female customers in their twenties to forties were allowed to continuously use using a ruby cell puff, and each of spreadability, moisturized feeling, coverage, makeup convenience, and makeup effect satisfaction in the first week, the third week, and the fifth week was investigated, and evaluation indexes are as follows:

1: Very bad
2: Bad
3: Moderate
4: Good
5: Very good

TABLE 4

|  | First week | | Third week | | Fifth week | |
|---|---|---|---|---|---|---|
|  | A | B | A | B | A | B |
| Spreadability | 3.7 | 4.2 | 3.2 | 4.0 | 2.8 | 4.1 |
| Moisturized feeling | 3.8 | 4.4 | 3.2 | 4.1 | 3.0 | 4.0 |
| Coverage | 3.6 | 4.3 | 2.9 | 4.1 | 2.4 | 3.9 |
| Makeup convenience | 3.6 | 4.5 | 3.0 | 4.3 | 2.5 | 4.2 |
| Makeup effect satisfaction | 3.7 | 4.4 | 3.0 | 4.2 | 2.6 | 4.1 |

As a result of the customer test, similar to experimental example 2, due to a high quantity dispensed, satisfaction with B was higher than the sponge impregnation material cosmetic ingredients and B obtained noticeably excellent results over time.

Experimental Example 4: Leakage Test at Varying Thickness of Film Forming Member Samples were prepared in which 15 g of the content prepared at the viscosity described in the above Table 1 was stored in the receiving member with the sheet-type member as shown in Table 2. When the container stands erect in a constant temperature tank of 25 degrees, a leakage test was conducted to determine whether the content flows out of the sheet-type film forming member and gets the container contaminated, or the content does not flows out and the container remains clean.

TABLE 5

| Cosmetic ingredient content film forming member | Example 1 | Example 2 | Example 3 | Comparative example 1 | Comparative example 2 |
|---|---|---|---|---|---|
| Example 4 | No leak | No leak | No leak | Leak occurred | No leak |
| Example 5 | No leak | No leak | No leak | Leak occurred | No leak |
| Example 6 | No leak | No leak | No leak | Leak occurred | No leak |
| Example 7 | No leak | No leak | No leak | Leak occurred | No leak |
| Comparative example 3 | Leak occurred | Leak occurred | Leak occurred | Leak occurred | Leak occurred |
| Comparative example 4 | Leak occurred | Leak occurred | Leak occurred | Leak occurred | No leak |
| Comparative example 5 | Leak occurred | Leak occurred | Leak occurred | Leak occurred | Leak occurred |

As a result of the leakage test, as can be seen from Table 5, in the case of examples, when the viscosity is 1000 cps or less like comparative example 1, or when the entire thickness is 0.4 mm or less like comparative examples 3, 4 and 5, leakage occurred in all, no matter whether the fibers of the film forming member are dense. As the viscosity of the cosmetic ingredients increases or the thickness of the film forming member increases, stability against leakage is high. However, when 3.0 mm or more is used like comparative example 6, leakage stability may be excellent but the thickness is too large, failing to tighten the same test container, and due to forced tightening, the content leaked out of the container at the time of content impregnation.

Experimental Example 5: Test of Sensorial Feeling vs Viscosity of the Content

A sample (example 5) was prepared by filling the container with the content prepared at the viscosity described in the above Table 1 and covering an opening with the film forming member. Changes in sensorial feeling at varying viscosity were compared together in twenty women aged twenties to forties, and evaluation indexes are the same as the method of experimental example 3.

TABLE 6

|  | Example 1 | Example 2 | Example 3 | Comparative example 1 | Comparative example 2 |
|---|---|---|---|---|---|
| Spreadability | 4.2 | 4.2 | 4.0 | 3.7 | 3.1 |
| Moisturized feeling | 4.3 | 4.2 | 4.2 | 3.8 | 2.8 |
| Coverage | 4.0 | 4.1 | 4.1 | 3.5 | 4.1 |
| Makeup convenience | 4.1 | 4.2 | 4.3 | 2.6 | 2.7 |
| Makeup effect satisfaction | 4.1 | 4.3 | 4.2 | 3.2 | 2.8 |

As can be seen from Table 6, in the case of the present disclosure, when viscosity is as low as 1000 cps or less like comparative example 1, during use by customers, makeup convenience and makeup effect satisfaction is found relatively much lower due to too low viscosity. Also, it can be seen that comparative example 2 having viscosity of 7000 cps or more has a significant reduction in sensorial feeling and makeup effect in all the items except coverage, when compared to example 1-3.

INDUSTRIAL APPLICABILITY

The present disclosure provides the cosmetic having excellent portability.

By the use of the elastic film forming member, the cosmetic of the present disclosure may provide convenience of carrying with, reduce the container volume, and increase an amount of cosmetic composition contained, as compared to sponge impregnation material cosmetics.

What is claimed is:

1. A cosmetic comprising:
    a low viscosity cosmetic composition;
    a receiving member in which the low viscosity cosmetic composition is received, wherein the receiving member has an opening; and
    a film forming member comprising a deformable pore structure,
    wherein the low viscosity cosmetic composition has a viscosity of from 1,000 cPs to 7,000 cPs,
    wherein the film forming member has a thickness of from 0.4 mm to 3.0 mm,
    wherein the film forming member is configured to dispense the low viscosity cosmetic composition upon application of a downward force,
    wherein the film forming member fully covers the opening of the receiving member,
    wherein the film forming member forms a water film or oil film on the surface of the cosmetic composition through contact with the low viscosity cosmetic composition, and
    wherein the film forming member is capable of preventing leakage of the cosmetic composition from the cosmetic, and
    wherein the low viscosity cosmetic composition is received in the receiving member without an impregnation material.

2. The cosmetic according to claim 1, wherein the cosmetic composition has viscosity of from 2,000 cPs to 6,000 cPs.

3. The cosmetic according to claim 1, wherein the film forming member is a reticulated structure having elasticity.

4. The cosmetic according to claim 1, wherein the film forming member is any one selected from the group consisting of a fiber fabric, a foam rubber sheet, a polyurethane foam sheet, and blends thereof.

5. The cosmetic according to claim 4, wherein the fiber fabric is any one selected from the group consisting of natural fiber, artificial fiber, and blends thereof.

6. The cosmetic according to claim 5, wherein the natural fiber is any one selected from the group consisting of cotton, kapok fiber, coier, manila hemp, sisal hemp, flax, ramie, jute, hemp, wool, goat hair, camel hair, cashmere, cultivated silk, wild silk, rock wool, and blends thereof.

7. The cosmetic according to claim 5, wherein the artificial fiber is any one selected from the group consisting of viscose rayon, cupra rayon, acetate, triacetate, nylon fiber, polyester fiber, polyurethane-based, polyurea-based, polyethylene-based, polyvinyl chloride-based, polyvinylidene-based, polytetrafluoroethylene-based, polyvinyl alcohol-based, polyacrylonitrile-based and polypropylene-based fibers and blends thereof.

8. The cosmetic according to claim 7, wherein the artificial fiber is a blend of a polyester-based fiber and spandex.

9. The cosmetic according to claim 4, wherein the foam rubber sheet is any one selected from the group consisting of natural rubber (NR), styrene butadiene rubber (SBR), modified styrene butadiene rubber, butadiene rubber (BR), modified butadiene rubber, chlorosulfonated polyethylene rubber, epichlorohydrin rubber, fluorocarbon rubber, silicone rubber, nitrile rubber, hydrogenated nitrile rubber, nitrile butadiene rubber (NBR), modified nitrile butadiene rubber, chlorinated polyethylene rubber, styrene butadiene styrene rubber (SBS), and blends thereof.

10. The cosmetic according to claim 4, wherein the polyurethane foam sheet is any one of polyether urethane, polybutadiene urethane, polyester urethane or blends thereof.

11. The cosmetic according to claim 1, wherein the cosmetic composition film forming member is a single layer or multiple layers.

* * * * *